United States Patent
Bakker et al.

(10) Patent No.: US 7,501,025 B2
(45) Date of Patent: Mar. 10, 2009

(54) PROCESS AND APPARATUS FOR THE CONVERSION OF BIOMASS

(75) Inventors: Robert Reurd C. Bakker, Wageningen (NL); Jacob Hendrik O. Hazewinkel, Zoetermeer (NL); Johannes Wouterus Van Groenestijn, Apeldoorn (NL)

(73) Assignees: Agrotechnology & Food Innovations B.V., Wageningen (NL); Nederlandse Organisatie voor Toegepast-Natuurwetenschappelijk Onderzoek TNO, Delft (NL); Techno Invent Ingenieursbureau voor Milieutechniek B.V., Zoetermeer (NL)

( * ) Notice: Subject to any disclaimer, the term of this patent is extended or adjusted under 35 U.S.C. 154(b) by 0 days.

(21) Appl. No.: 11/837,156

(22) Filed: Aug. 10, 2007

(65) Prior Publication Data
US 2008/0022997 A1     Jan. 31, 2008

Related U.S. Application Data

(63) Continuation of application No. PCT/NL2006/000073, filed on Feb. 13, 2006.

(30) Foreign Application Priority Data
Feb. 11, 2005    (EP)    .................. 05075352

(51) Int. Cl.
| | |
|---|---|
| *C13K 1/02* | (2006.01) |
| *B01J 3/00* | (2006.01) |
| *B01D 21/01* | (2006.01) |
| *B01D 19/00* | (2006.01) |
| *B01D 53/14* | (2006.01) |
| *B03D 3/00* | (2006.01) |
| *C07G 17/00* | (2006.01) |
| *C07H 1/00* | (2006.01) |
| *C07H 3/00* | (2006.01) |

(52) U.S. Cl. ............................. 127/37; 127/1; 210/724; 536/124; 95/171

(58) Field of Classification Search .................... 127/37, 127/1; 210/724; 536/124; 95/171
See application file for complete search history.

(56) References Cited

U.S. PATENT DOCUMENTS

| | | | | |
|---|---|---|---|---|
| 3,297,676 A | | 1/1967 | Brauns ..................... 260/124 |
| 4,242,455 A | | 12/1980 | Muller et al. ............... 435/162 |
| 4,304,608 A | * | 12/1981 | Regnault et al. ............... 127/1 |
| 4,427,453 A | | 1/1984 | Reitter ......................... 127/1 |
| 4,427,584 A | * | 1/1984 | LeGrand et al. ............. 530/500 |
| 5,188,673 A | | 2/1993 | Clausen et al. ................ 127/37 |
| 5,424,417 A | * | 6/1995 | Torget et al. .................. 536/56 |
| 5,487,835 A | * | 1/1996 | Shane ....................... 210/749 |
| 5,562,777 A | | 10/1996 | Farone et al. ................. 127/37 |
| 5,580,389 A | | 12/1996 | Farone et al. .............. 127/46.2 |
| 5,597,714 A | | 1/1997 | Farone et al. ............... 435/100 |
| 5,620,877 A | | 4/1997 | Farone et al. ............... 435/139 |
| 5,641,337 A | * | 6/1997 | Arrowsmith et al. ........... 95/39 |
| 5,726,046 A | * | 3/1998 | Farone et al. ............... 435/100 |
| 5,782,982 A | | 7/1998 | Farone et al. ................. 127/37 |
| 5,820,687 A | | 10/1998 | Farone et al. .............. 127/46.2 |
| 5,935,300 A | * | 8/1999 | Niekerk ....................... 95/212 |
| 6,054,611 A | | 4/2000 | Farone et al. ............... 562/515 |
| 6,239,198 B1 | | 5/2001 | Abächerli et al. ............. 524/74 |
| 2002/0059994 A1 | | 5/2002 | Kurple ......................... 169/29 |

FOREIGN PATENT DOCUMENTS

| | | |
|---|---|---|
| WO | WO 94/23071 | 10/1994 |
| WO | WO 01/32715 | 5/2001 |
| WO | WO 2004/015145 | 2/2004 |

* cited by examiner

*Primary Examiner*—Karl E Group
*Assistant Examiner*—Noah S Wiese
(74) *Attorney, Agent, or Firm*—Banner & Witcoff, Ltd.

(57) ABSTRACT

The invention is directed to a process for the conversion of cellulosic biomass, in particular lignocellulose-containing biomass into fermentable sugars. The invention is further directed to apparatus suitable for carrying out such processes. According to the invention biomass is converted into fermentable sugars by contacting in a reactor said biomass with an acid, while passing an inert gas stream capable of taking up water through said reactor, by which the pH in said reactor can be controlled.

17 Claims, No Drawings

US 7,501,025 B2

PROCESS AND APPARATUS FOR THE CONVERSION OF BIOMASS

RELATED APPLICATIONS

This application is a continuation of PCT application no. PCT/NL2006/000073, designating the United States and filed Feb. 13, 2006; which claims the benefit of the filing date of European application no. 05075352.4, filed Feb. 11, 2005; each of which is hereby incorporated herein by reference in its entirety for all purposes.

FIELD

The invention is directed to a process for the conversion of biomass, in particular the conversion of lignocellulose-containing biomass into fermentable sugars. The invention is further directed to apparatus suitable for carrying out such processes.

BACKGROUND

Renewable materials will play an increasingly important role in the future. Biological conversion processes will be important in producing valuable products, such as ethanol, from renewable starting materials, such as biomass. A bottleneck in converting biomass is formed by the step in which the release of carbohydrates from lignocellulose, which is the main constituent of biomass, is to be carried out. In order to allow biocatalysts (e.g. microorganisms) access to the starting material, it is necessary to depolymerize and/or decrystallize the lignocellulose.

A known technique for this purpose is strong acid treatment, which is described for instance in U.S. Pat. Nos. 5,562,777, 5,580,389, 5,597,714, 5,620,877, 5,726,046, 5,782,982, 5,820,687, 6,054,611 and 6,239,198.

WO-A-94/23071 describes a method for producing sugars from materials containing cellulose and hemicellulose. The method comprises decrystallization and hydrolysis of the cellulose and hemicellulose with an acid and separation of the hydrolysate into sugars and acid.

U.S. Pat. No. 4,427,584 describes a stepwise process for converting crystalline α-cellulose to amorphous α-cellulose with liquid or gaseous sulphur trioxide to cause decrystallization of the α-cellulose followed by hydrolysis of the treated fibers to produce sugars.

The known techniques for converting cellulosic materials into fermentable products usually require the presence of a mechanical stirring device to obtain sufficient mixing of the cellulosic material and the strong acid. In practice this often leads to complications, because of the combination of moving parts and strong acid, which gives rise to corrosion problems. The cellulosic materials also generally require mechanical pretreatment to obtain the required particle size (usually 10 mm in diameter, or less), and water content (in general less than 10%).

Furthermore, the known techniques require chopping or grinding of the cellulosic materials to a particle size not greater than 10 mesh, in order to overcome the difficulty of providing good contact between the strong acid and the cellulosic material. This small particle size is also required to allow for suspension of the cellulosic materials in a hot air stream.

Furthermore, a separate evaporator is necessary to produce concentrated acid. This results in extra investment costs.

Furthermore, the known techniques referred to require a considerable amount of acid, which is subsequently neutralized using an appropriate amount of base. This leads to considerable streams of waste, such as gypsum, that need to be disposed of and thus incur costs.

SUMMARY

The present invention seeks to overcome these problems associated with prior art techniques, as well as other problems as will become apparent hereinbelow.

It was found that this objective can be met by providing a process in which a packed bed or heap of biomass is brought into contact with acid, and with a gas as the continuous phase. During this process, the biomass is broken down to a particle size of 10 mm or larger. Preferably, the contacting is carried out by cocurrently contacting the biomass with acid and countercurrently with a gas. The biomass may be mixed with an inert material with a large specific surface such as plastic pall rings to warrant the required structural strength of the packed biomass and ensure a good distribution of gas and liquid. Thus, in one aspect, the present invention is directed to a process for converting biomass into fermentable sugars comprising contacting in a reactor said biomass with an acid, while passing a gas stream through said reactor, wherein said gas is an inert gas which is able to take up water, thereby effectively changing the pH in the reactor.

DETAILED DESCRIPTION

By passing the gas stream through the reactor, evaporation of water from the acid solution can be changed and the acid concentration and thus the pH and the moisture content can effectively be controlled. In addition, the gas stream assists in providing a homogeneous distribution of acid throughout the reactor, without requiring mechanical stirring means. The acid used may be any strong acid known in the art to be suitable for this purpose, such as hydrochloric acid, phosphoric acid, hydrofluoric acid and sulphuric acid. Sulphuric acid is most preferred, because it may be removed using biological processes. Moreover, sulphuric acid may be employed in the form of (gaseous) sulphur trioxide that is added to the aqueous phase present in the reactor.

After the biomass is loaded into the reactor the acid is added, e.g. by spraying it from the top of the reactor. Optionally or alternatively $SO_3$ is added. If desired, water can be added so that an aqueous phase having the desired acid concentration is obtained. Subsequently the gas is fed, preferably from the bottom of the reactor. The acid used in the reactor may be recirculated back into the reactor, depending on the degree of depolymerization of the biomass. Also the gas stream is circulated. The gas flow rate may be adjusted so that the pH of the solution, which may be constantly monitored e.g. by means of pH electrodes, is kept at the desired level. Preferably the concentration of the acid is controlled at 70-75 wt. %, based on the weight of acid (expressed as kg $H_2SO_4$ per kg dry cellulosic material) and water present in said reactor.

In this way, the depolymerisation can be carried out at a more or less constant and high acid concentration. By result, the lignocellulose is converted into a viscous slurry which flows downwards to the bottom of the reactor, where it may be collected. After a sufficient amount of time the product containing depolymerized cellulose and hemicellulose may be removed from the reactor and fed to a subsequent processing step, optionally after a sieving step to remove coarse unconverted parts. The depolymerization process is generally carried out in a batch process. It may also be carried out in a semi-continuous manner: biomass is fed into the reactor while the gas and acid are circulated, until the volume of unconverted matter is such its removal from the reactor is required.

Another advantage of the process of the present invention is that non-converted material, which is often formed by contamination in the biomass feed (such as sand or pieces of plastic), remains in the reactor, and can be removed therefrom relatively easily after the reaction is completed.

The acid consumption of the process of the present invention is minimized. Furthermore, even large pieces of biomass, such as large chunks of wood, may be converted effectively. Because the acid concentration and moisture content can be controlled relatively easily by the process of the present invention, the type of feed that can be used may vary widely in water content, which adds to the versatility of the process.

The gas that is used for passing through the reactor may in principle be any gas that is able to take up water in a sufficient amount. The gas is inert with respect to the acid treatment process, i.e. it does not interfere with the acid treatment process. Preferably this gas comprises $CO_2$ (typically more than 90 vol. %, e.g. more than 99 vol. %), because $CO_2$ can be obtained from a subsequent fermentation step, in which the biomass that is converted by the acid treatment is converted to e.g. ethanol. Another advantage of $CO_2$ is that it helps to suppress the formation of undesired products, in particular oxidation products. Other gases suitable gases include nitrogen ($N_2$) and air. Thus the gas stream comprises preferably a component selected from the group consisting of $CO_2$, nitrogen, air, and combinations thereof. Because of the low pH in the reactor, air will be more or less inert vis-à-vis the reactor contents as well.

In view of process economics, it is preferred to circulate the gas stream. This involves removing water from the gas stream before it is fed back to the reactor. Water may be removed using known techniques, such as cooling to a sufficiently low temperature. It was found that a temperature of ca. 0-4° C., provides for a gas that is sufficiently dry. Good results are obtained with a temperature of about 2° C.

The acid used in the reactor is preferably sulphuric acid. This can be fed as concentrated $H_2SO_4$ (e.g. 90 wt. % or more) to the reactor, but it is also possible to have sulphuric acid formed in situ by adding sulphur trioxide gas to the reactor, which yields sulphuric acid when dissolved in water: $SO_3 + H_2O \rightarrow H_2SO_4$. The sulphur trioxide may be obtained from a different process step in which sulphur compounds are burnt using oxygen or air. Preferably such a sulphur compound is hydrogen sulphide, which can be obtained from a sulphate reduction step that may be employed to remove sulphur compounds from the products.

In a typical embodiment, the gas velocity through the bed is kept relatively low (e.g. below 0.5 m/s) so that the pressure drop across the bed is limited (e.g. to about 50 mm $H_2O$).

The pressure in the reactor can be atmospheric, or slightly higher.

The temperature in the reactor is preferably from 60-100° C., more preferably from 75-85° C., since this already provides for a suitable rate of reaction, while at the same time excessive evaporation of water is avoided.

The amount of acid is low. Preferably less than 2 kg acid per kg of dry matter is present, more preferably 1.2-1.4 kg $H_2SO_4$ per kg of dry matter. The prior art techniques for treatment of biomass with strong acids generally employs much more acid than 2 kg acid per kg of dry matter.

In the process of the present invention the concentration of the acid is preferably controlled at 70-75 wt. %, based on the weight of acid (expressed as kg $H_2SO_4$ per kg of dry matter) and water present in said reactor.

It is possible to obtain a good chemical conversion when the residence time of the reactor contents is set to 10 to 14 hours, preferably about 12 hours.

An apparatus for carrying out the process of the present invention typically comprise a non-stirred batch reactor vessel, which may conveniently be constructed of concrete (which is cheap and robust), which is provided on the inside with an acid resistant lining, such as a Teflon™ lining or a PVC lining. The reactor is further provided with gas entry and gas exit means, as well as means for feeding acid, in particular one or more spraying nozzles for distributing acid solution. The equipment may further comprise a heater for heating the gas entry stream before it enters the reactor. During operation the lignocellulose depolymerises and forms a slurry. The slurry moves downward and is collected in the bottom part of the reactor. The apparatus for carrying out the invention may further comprise a pump for pumping out the slurry from the reactor. It may further comprise one or more sieves to remove course parts from the product stream.

The product obtained from the process of the present invention, may be further processed in subsequent steps. Typically this involves the addition of water which effects the hydrolysis of the depolymerized cellulose and hemicellulose into oligomeric or monomeric sugars. In this step the lignin may be precipitated and can be filtered off in a filtration step. Carbonate and bicarbonate that is present in the solution is converted into $CO_2$, which may be collected at the top of the reactor wherein this step is carried out. This $CO_2$ stream may be used for passing through the reactor where the biomass is hydrolysed to oligomeric or monomeric sugars.

The invention claimed is:

1. A process for conversion of cellulosic biomass into fermentable sugars comprising contacting a packed bed or heap of said biomass in a reactor with an acid, while passing a gas stream though said reactor, wherein said gas is an inert gas which is able to take up water, thereby effectively changing the pH in the reactor.

2. The process according to claim 1, wherein said gas comprises CO2, air, nitrogen, or combinations thereof, with greater than 90 vol. % CO2.

3. The process according to claim 1, wherein said gas stream is circulated.

4. The process according to claim 1, wherein said gas stream is cooled, by which water condenses therefrom, and a dry gas stream is obtained, which is subsequently fed to said reactor.

5. The process according to claim 1, wherein said biomass contains large chunks or coarse particles with an average particle size of equal to or larger than 10 mm.

6. The process according to claim 1, wherein the temperature in said reactor is from 60-100° C.

7. The process according to claim 1, wherein the concentration of the acid is controlled at 70-75 wt. %, based on the weight of acid and water present in said reactor.

8. The process according to claim 1, wherein the residence time in said reactor is 10 to 14 hours.

9. The process according to claim 1, wherein said acid is sulphuric acid.

10. The process according to claim 9, wherein at least part of said sulphuric acid is obtained by feeding SO3 to said reactor.

11. The process according to claim 9, wherein 1-2 kg H2SO4 per kg of dry matter is present.

12. An apparatus for converting cellulosic biomass into fermentable sugars comprising a non-stirred batch reactor vessel in which a packed bed or heap of said biomass is brought into contact with an acid, which is provided on the inside with an acid resistant lining, and further provided with gas entry and gas exit means, as well as means for feeding acid.

13. The apparatus according to claim 12, which is constructed of concrete.

14. The apparatus according to claim 12, wherein said means for feeding acid comprise one or more spraying nozzles.

15. The process according to claim 1, wherein the temperature in said reactor is from 75-85° C.

16. The process according to claim 1, wherein the residence time in said reactor is about 12 hours.

17. The process according to claim 9, wherein 1.2-1.4 kg H2SO4 per kg of dry matter is present.

* * * * *